United States Patent
Menn (10) Patent No.: US 10,589,037 B1
(45) Date of Patent: Mar. 17, 2020

(54) INJECTION NEEDLE FOR PREVENTING TISSUE CORING

(71) Applicant: Pavel Menn, Marblehead, MA (US)

(72) Inventor: Pavel Menn, Marblehead, MA (US)

( * ) Notice: Subject to any disclaimer, the term of this patent is extended or adjusted under 35 U.S.C. 154(b) by 0 days.

(21) Appl. No.: 16/427,643

(22) Filed: May 31, 2019

(51) Int. Cl.
  *A61M 5/32* (2006.01)
  *A61M 25/00* (2006.01)

(52) U.S. Cl.
  CPC ......... *A61M 5/3286* (2013.01); *A61M 25/007* (2013.01); *A61M 2205/195* (2013.01)

(58) Field of Classification Search
  CPC .............. A61M 25/007; A61M 5/3286; A61M 2025/0073; A61M 2205/195; A61M 5/158; A61M 2205/0073; A61B 17/3417
  See application file for complete search history.

(56) References Cited

U.S. PATENT DOCUMENTS

2012/0083727 A1* 4/2012 Barnett ................. A61F 9/0017
                                                                604/22

* cited by examiner

*Primary Examiner* — Bhisma Mehta
*Assistant Examiner* — Hamza A Darb
(74) *Attorney, Agent, or Firm* — Daniel N. Smith (57) ABSTRACT

This invention relates to an injection needle with a multi-surface penetration end which stretches soft tissue with minimal cutting upon insertion. This stretching reduces patient discomfort, the force required for urging needle into the soft tissue, and soft tissue coring. The structure of the multi-surface needle decreases the penetration footprint of the needle into the soft tissue around the needle penetration site, reducing tissue inflammation and increasing healing time. The needle also contains dual injection openings on opposing sides, behind the penetration end to discharge injected fluid over a wider area with lower pressure.

12 Claims, 12 Drawing Sheets

INJECTION NEEDLE FOR PREVENTING TISSUE CORING

FIELD OF THE INVENTION

This invention relates to an injection needle with a multi-surface penetration end stretches soft tissue with minimal cutting to reduce patient discomfort, reduces the force required for urging needle into the soft tissue, prevents soft tissue coring, and contains dual injection openings behind the penetration points to spread out injected fluid.

BACKGROUND OF INVENTION

A hypodermic injection needle is typically formed from an elongated tube having a fluid-conducting lumen and a sharpened end for penetrating soft epidermis, flesh, or tissue to inject fluid.

Injection needle designs usually require excessive penetration force to urge the needle end through the soft tissue for dispensing fluid. Furthermore, injection needles often cause soft tissue coring, or when a portion of the penetrated soft tissue through becomes lodged in the lumen adjacent the needle end. Higher penetration force and tissue coring requires the fluid to be injected under higher pressure.

All of these problems result in patient discomfort, patient pain, tissue inflammation, longer healing times, and the inefficient dispersal of injected fluid.

This invention solves these problems with an injection needle with a multi-surface penetration end which stretches soft tissue with minimal cutting upon insertion.

This stretching reduces patient discomfort, the force required for urging needle into the soft tissue, and soft tissue coring. The structure of the multi-surface needle decreases the penetration footprint of the needle into the soft tissue around the needle penetration site, reducing tissue inflammation and increasing healing time. The needle also contains dual injection openings on opposing sides, behind the penetration end to discharge injected fluid over a wider area with lower pressure.

SUMMARY OF THE INVENTION

There are additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

The subject invention discloses a medical needle for penetrating soft tissue and dispensing fluid, the needle comprising: a proximal end tube with a central axis comprising an internal fluid-carrying lumen, a multi-surface distal end comprising a soft tissue penetrating apex substantially aligned with the central axis; two primary surfaces extending proximally from apex, wherein the primary surfaces are substantially symmetrical with each other and formed on opposing sides of the apex about the central axis, wherein the two primary surfaces comprise outward edges; a first intersect edge extending proximally from the apex and connecting the two primary surfaces, wherein the first intersect edge is substantially aligned with the central axis; a central surface directly proximal from the first intersect edge and between the two primary surfaces, wherein the central surface and the two primary surfaces are connected at a first intersect point and two second intersect edges demarcating the respective planes of the central surface and the two primary surfaces, a top fluid opening directly proximal from the central surface, wherein the top fluid opening extends to a bottom fluid opening, wherein the top and bottom fluid openings are substantially aligned and are in fluid communication with the internal fluid-carrying lumen of the tube; two secondary surfaces on opposing sides of the top fluid opening about the central axis, wherein the secondary surfaces are substantially symmetrical with each other, wherein the two secondary surfaces and the two primary surfaces are connected at third intersect edges demarcating the respective planes of the two secondary surfaces and the two primary surfaces, further wherein the two secondary surfaces and the central surface are connected at fourth intersect edges demarcating the respective planes of the two secondary surfaces and the central surface; wherein the multiple surfaces of the distal end of the needle stretch the soft tissue at a penetration point of the apex as the needle into inserted into the soft tissue; and wherein the distal end of the needle is inserted into the soft tissue until the top and bottom fluid openings are within the soft tissue, wherein fluid is injected from the internal fluid-carrying lumen of the tube simultaneously through the top and bottom fluid openings into the soft tissue.

The subject invention also discloses a medical needle for penetrating soft tissue and dispensing fluid, the needle comprising: a proximal end tube with a central axis comprising an internal fluid-carrying lumen, a multi-surface distal end comprising a soft tissue penetrating apex substantially aligned with the central axis; two primary surfaces extending proximally from apex, wherein the primary surfaces are substantially symmetrical with each other and formed on opposing sides of the apex about the central axis, wherein the two primary surfaces comprise curved edges extending outwardly from the central axis, further wherein the curved edges extend to a width greater than a width of the tube; a first intersect edge extending proximally from the apex and connecting the two primary surfaces, wherein the first intersect edge is substantially aligned with the central axis; a secondary central surface directly proximal from the first intersect edge and between the two primary surfaces, wherein the secondary central surface and the two primary surfaces are connected at a first intersect point and two second intersect edges demarcating the respective planes of the secondary central surface and the two primary surfaces, a top fluid opening directly proximal from the secondary central surface, wherein the top fluid opening extends to a bottom fluid opening, wherein the top and bottom fluid openings are substantially aligned and are in fluid communication with the internal fluid-carrying lumen of the tube; two tertiary surfaces on opposing sides of the top fluid opening about the central axis, wherein the tertiary surfaces are substantially symmetrical with each other, wherein the two tertiary surfaces and the two primary surfaces are connected at third intersect edges demarcating the respective planes of the two tertiary surfaces and the two primary surfaces, further wherein the two tertiary surfaces and the secondary central surface are connected at fourth intersect edges demarcating the respective planes of the two tertiary surfaces and the secondary central surface; wherein the two primary surfaces, the curved edges of the two primary surfaces, the first intersect edge, the secondary central surface, the first intersect point, the two second intersect edges, the two tertiary surfaces, the two third intersect edges, and the two fourth intersect edges all stretch the soft tissue at a penetration point of the apex as the needle into inserted into the soft tissue; and wherein the distal end of the needle is inserted into the soft tissue until the top and bottom fluid openings are within the soft tissue, wherein fluid is injected from the internal fluid-carrying lumen of the tube simultaneously through the top and bottom fluid openings into the soft tissue.

In embodiments of the subject invention, the distal end of tube expands outwardly in the distal direction.

In further embodiments of the subject invention, the distal end of the needle stretches penetrated tissue 0.3 to 0.6 inches.

In other embodiments of the subject invention, the distal end of the needle stretches penetrated tissue 0.3 to 0.6 cm.

In additional embodiments of the subject invention, the distal end of the needle comprises a substantially trapezoidal-shaped cross section that forms into a substantially triangular-shaped cross section in the distal direction.

In embodiments of the subject invention, the two primary surfaces comprise gradually curved surfaces.

In further embodiments of the subject invention, the multiple surfaces of the distal end of the needle do not cut the soft tissue after the apex penetrates the soft tissue and the needle is inserted.

In other embodiments of the subject invention, the two primary surfaces, the curved edges of the two primary surfaces, the first intersect edge, the secondary central surface, the first intersect point, the two second intersect edges, the two tertiary surfaces, the two third intersect edges, and the two fourth intersect edges all do not cut the soft tissue after the apex penetrates the soft tissue and the needle is inserted.

In embodiments of the subject invention, the multiple surfaces of the distal end of the needle do not core the soft tissue after the apex penetrates the soft tissue and the needle is inserted.

In embodiments of the subject invention, the two primary surfaces, the curved edges of the two primary surfaces, the first intersect edge, the secondary central surface, the first intersect point, the two second intersect edges, the two tertiary surfaces, the two third intersect edges, and the two fourth intersect edges all do not core the soft tissue after the apex penetrates the soft tissue and the needle is inserted.

In embodiments of the subject invention, the needle further comprises two quaternary surfaces on opposing sides of the fluid openings about the central axis, wherein the two quaternary surfaces substantially symmetrical with each other; wherein the two quaternary surfaces and the two primary surfaces are connected at fifth intersect edges demarcating the respective planes of the two quaternary surfaces and the two primary surfaces, wherein the two primary surfaces, the curved edges of the two primary surfaces, the first intersect edge, the secondary central surface, the first intersect point, the second intersect edges, the two tertiary surfaces, the third intersect edges, the fourth intersect edges, the two quaternary surfaces, and the fifth intersect edges all stretch the soft tissue at a penetration point of the apex as the needle into inserted into the soft tissue; and wherein the distal end of the needle is inserted into the soft tissue until the top and bottom fluid openings are within the tissue, wherein fluid is injection from the internal fluid-carrying lumen of the tube simultaneously through the top and bottom fluid openings into the soft tissue.

In another embodiment of the subject invention, the needle may be composed of titanium, stainless steel, or any other suitable metal.

In embodiments of the subject invention, the term "substantially" is defined as at least close to (and can include) a given value or state, as understood by a person of ordinary skill in the art. In one embodiment, the term "substantially" refers to ranges within 10%, preferably within 5%, more preferably within 1%, and most preferably within 0.1% of the given value or state being specified.

In embodiments of the subject invention, the term "distal" denotes a direction, or end, closest the injection point of the needle, and the term "proximal" denotes a direction, or end furthest from the injection point of the needle.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto. These together with other objects of the invention, along with the various features of novelty, which characterize the invention, are pointed out with particularity in the claims annexed to and forming a part of this disclosure.

BRIEF DESCRIPTION OF THE DRAWINGS

Advantages of the present invention will be apparent from the following detailed description of embodiments thereof, which description should be considered in conjunction with the accompanying drawings, in which.

DETAILED DESCRIPTION OF THE EMBODIMENTS

While several variations of the present invention have been illustrated by way of example in particular embodiments, it is apparent that further embodiments could be developed within the spirit and scope of the present invention, or the inventive concept thereof. However, it is to be expressly understood that such modifications and adaptations are within the spirit and scope of the present invention, and are inclusive, but not limited to the following appended claims as set forth.

The subject invention comprises a hypodermic needle 1, as shown in FIGS. 1-12. The needle 1 comprises a proximal end 2 having a tube 3 with a central axis 4. The tube 3 contains an internal fluid-carrying lumen 5 for injecting fluid medications.

The needle 1 comprises a multi-surface distal end 6 that penetrates and stretches soft tissue with minimal cutting to reduce patient discomfort or pain. The structure of the multi-surface distal end 6 of the needle 1 reduces the force required for urging the multi-surface distal end 6 into the soft tissue. The structure of the multi-surface distal end 6 of the needle 1 also prevents soft tissue coring. The structure of the multi-surface distal end 6 substantially decreases the penetration footprint of the needle 1 into the soft tissue around the needle penetration site, substantially reducing tissue inflammation and increasing healing time.

The multi-surface distal end 6 of the needle 1 comprises a proximal end 7 that is an expanding tube 8, expanding outwardly from the distal end of tube 3 to a tissue penetration line 9 on the multi-surface distal end 6. The tissue penetration line 9 is the widest point of the multi-surface distal end 6 of the needle 1.

The multi-surface distal end 6 of the needle 1 comprises a distal end apex 10 or tissue penetration point. Two primary surfaces 11 extend proximally on opposing sides from the distal end apex 10 about the fluid opening 26. The two primary surfaces 11 contain a first intersect edge 12 that extends proximally from the apex 10, and is substantially aligned with the central axis 4. The two primary surfaces 11 are substantially symmetrical with each other on either side of the multi-surface distal end 6. In embodiments of the subject invention, the two primary surfaces 11 may be substantially flat or gradually curved.

Figure 1:
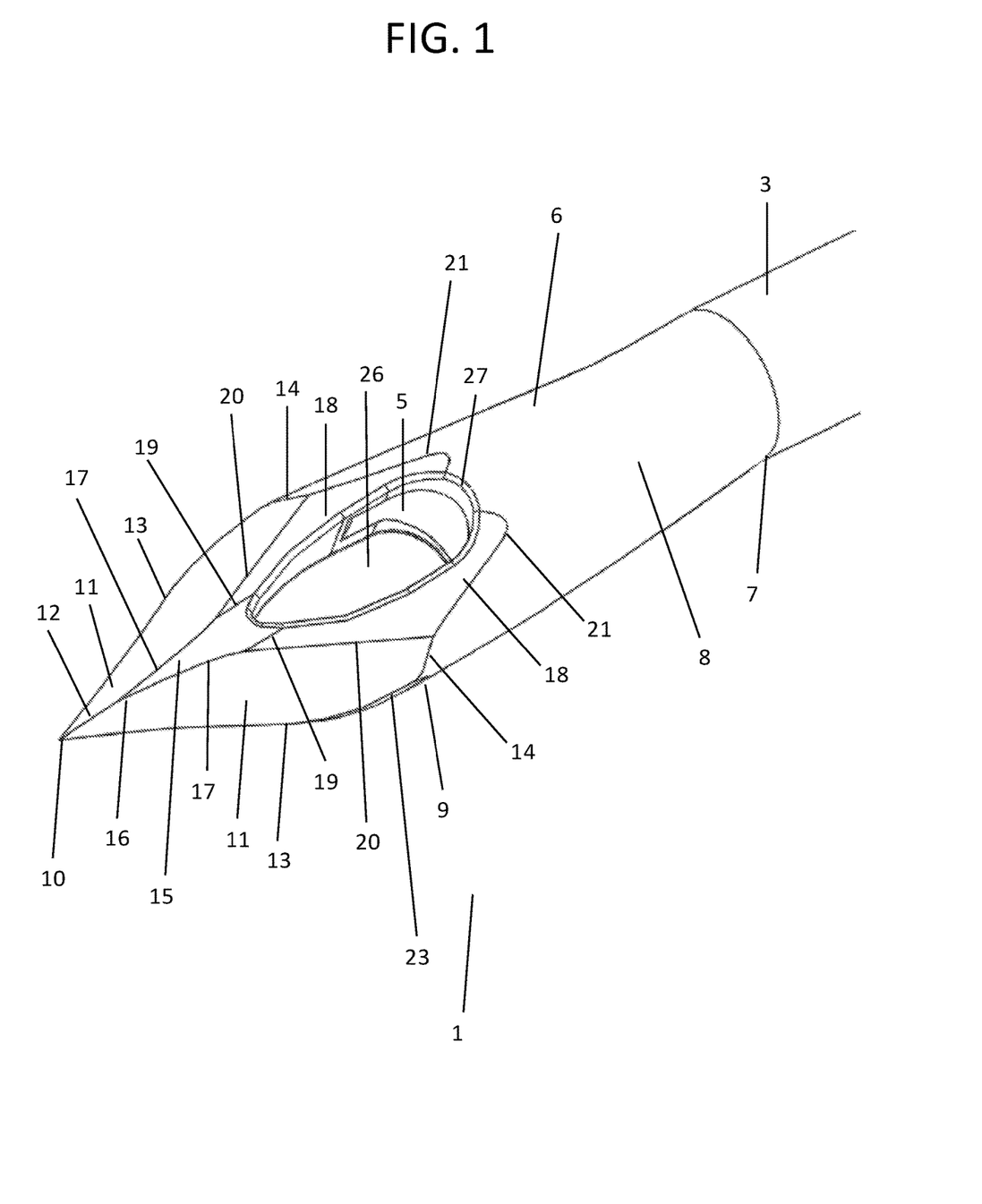
FIG. 1 illustrates a perspective view of the distal end of a hypodermic injection needle of the subject invention.
Figure 2:
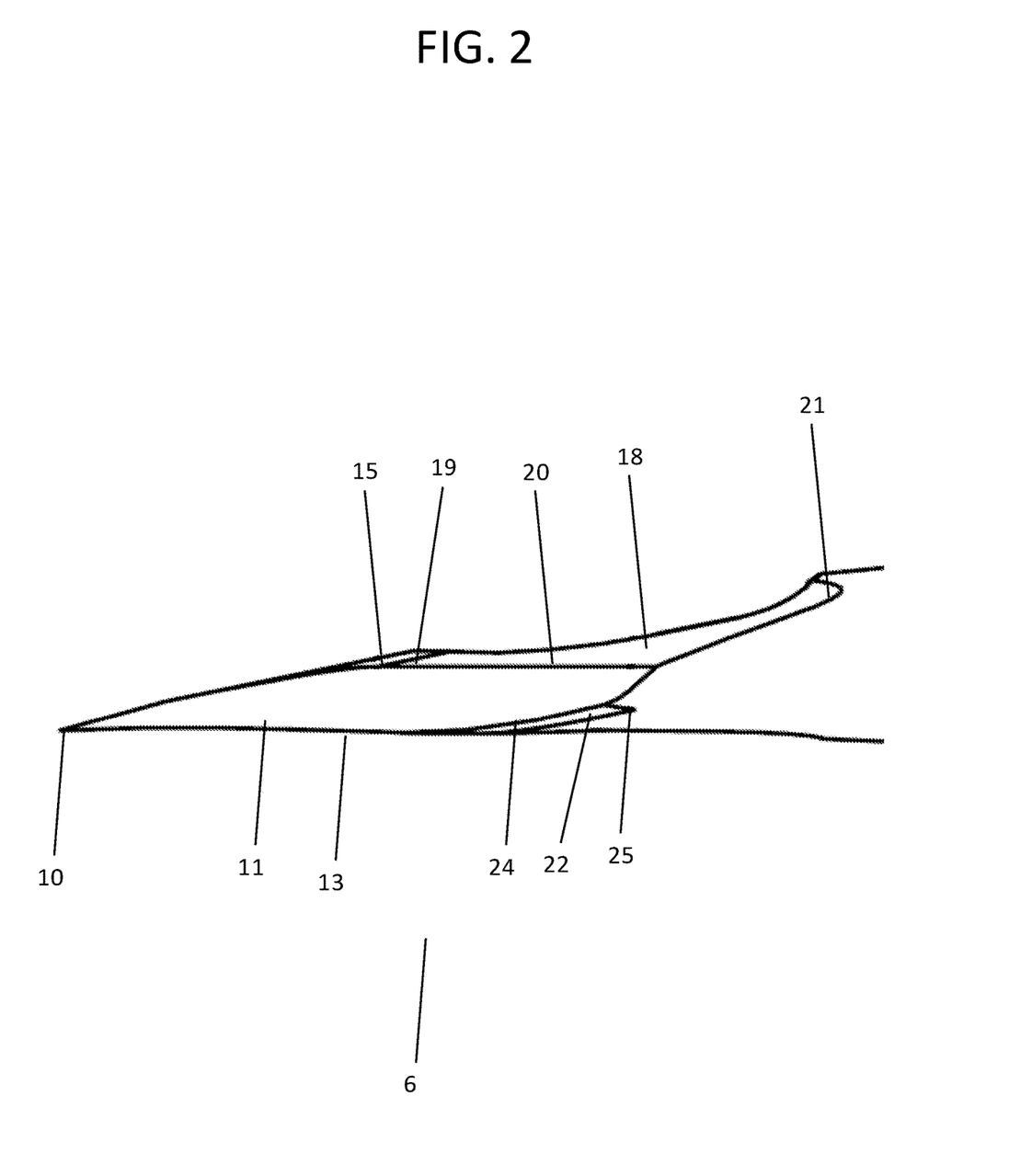
FIG. 2 illustrates a side view of the distal end of the hypodermic injection needle.
Figure 3:
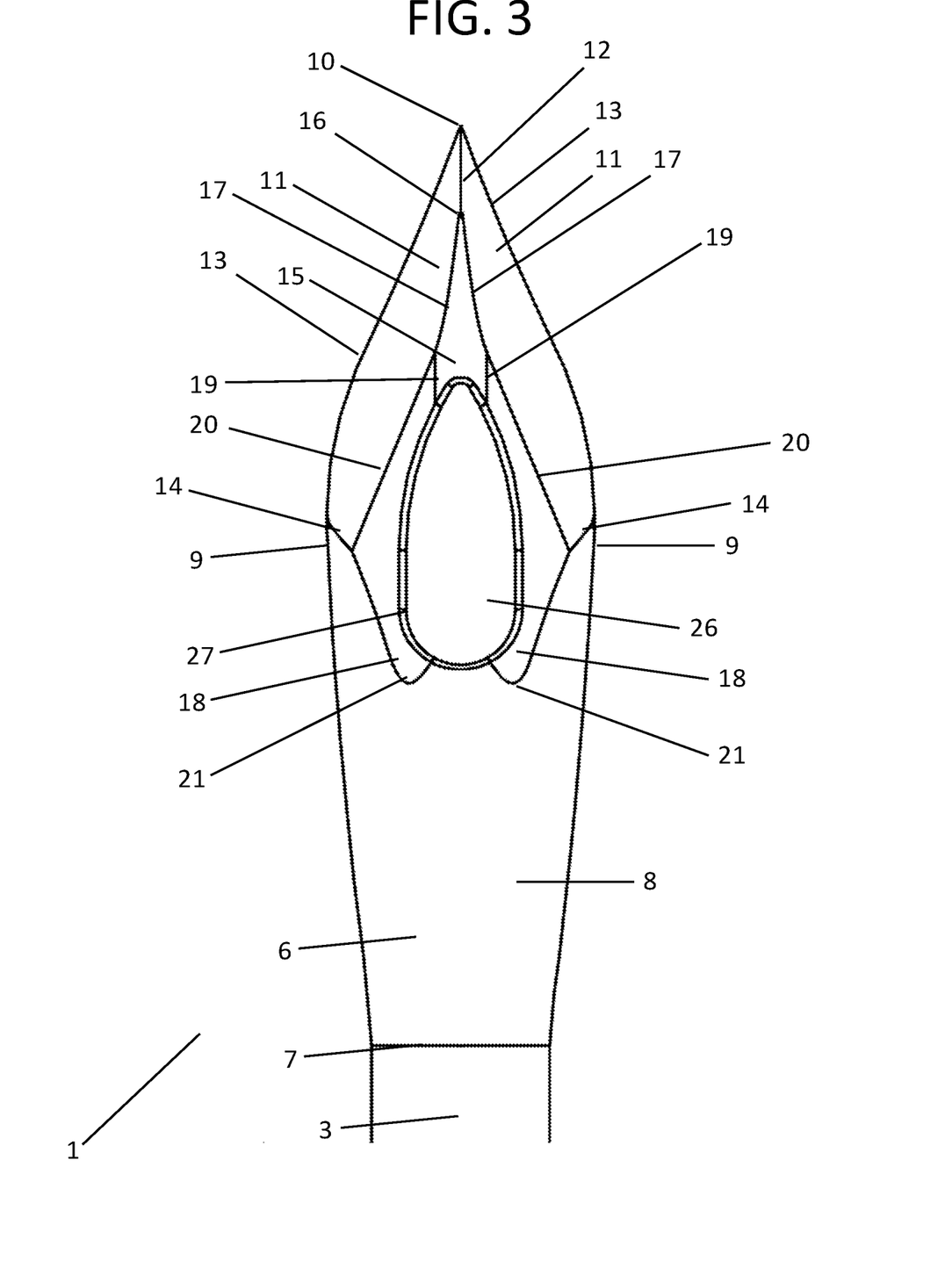
FIG. 3 illustrates a top view of the distal end of the hypodermic injection needle.
Figure 4:
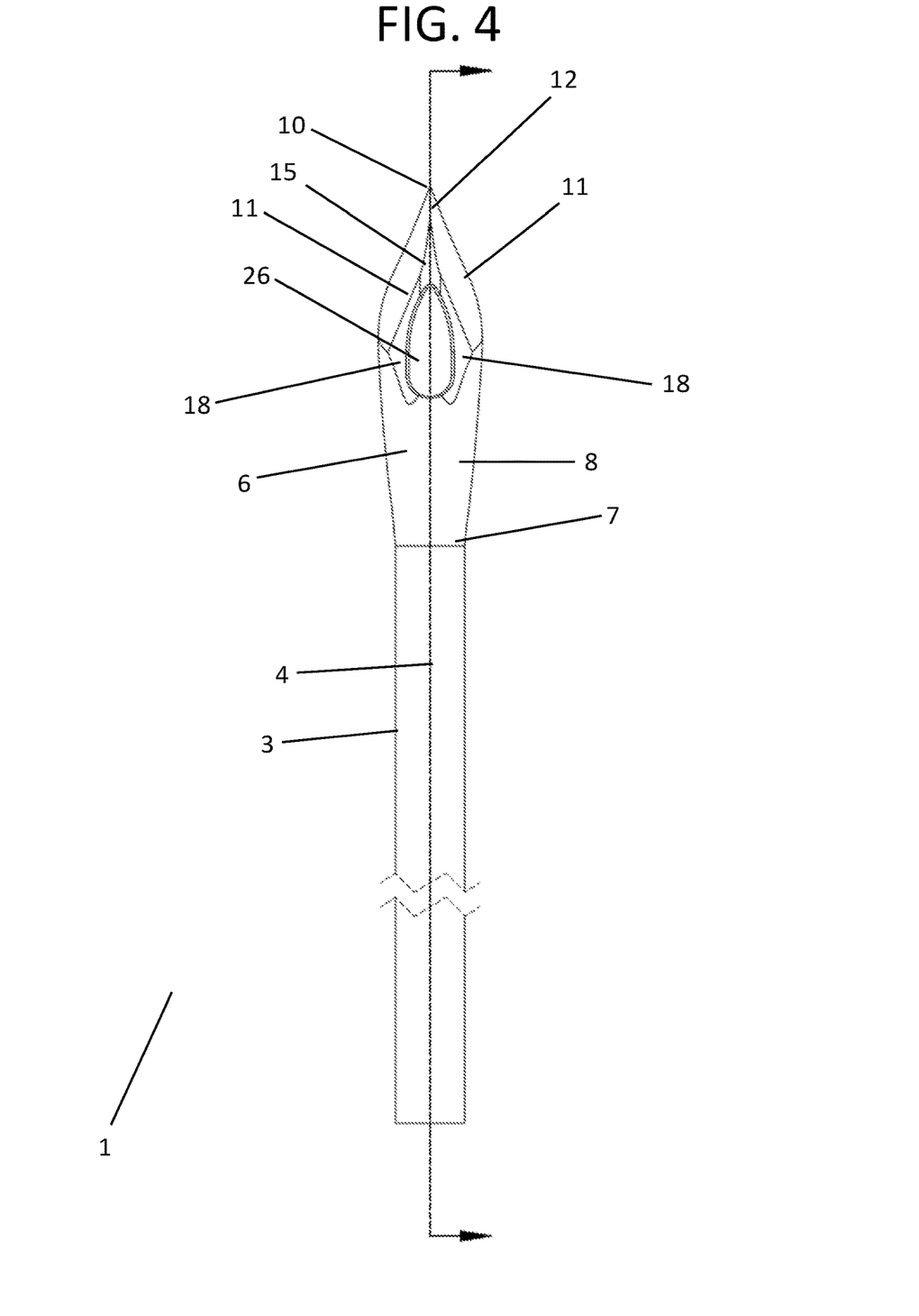
FIG. 4 illustrates a top view of the hypodermic injection needle.
Figure 5:
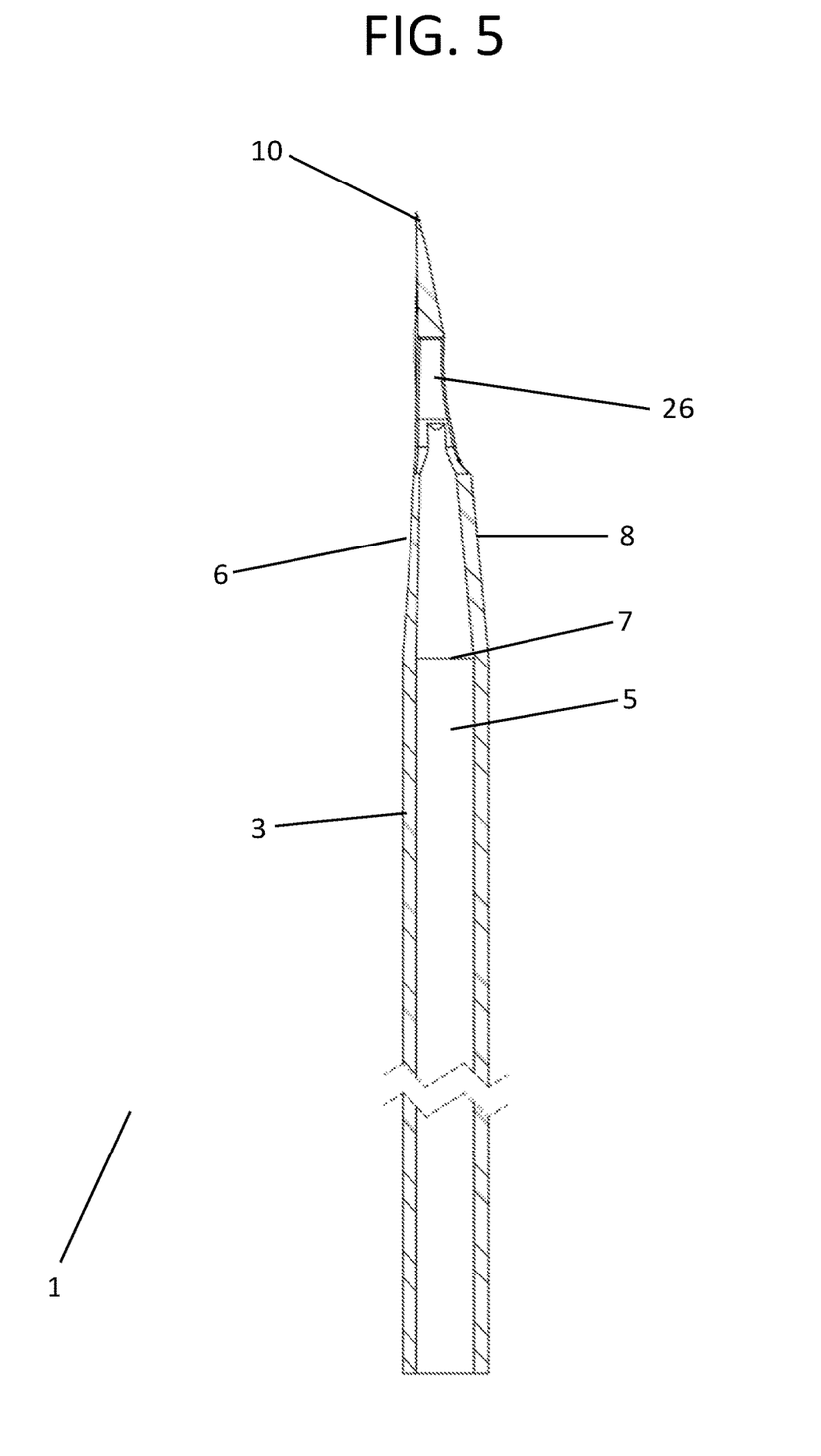
FIG. 5 illustrates a side cross sectional view of the hypodermic injection needle along line A-A of FIG. 4.
Figure 6:
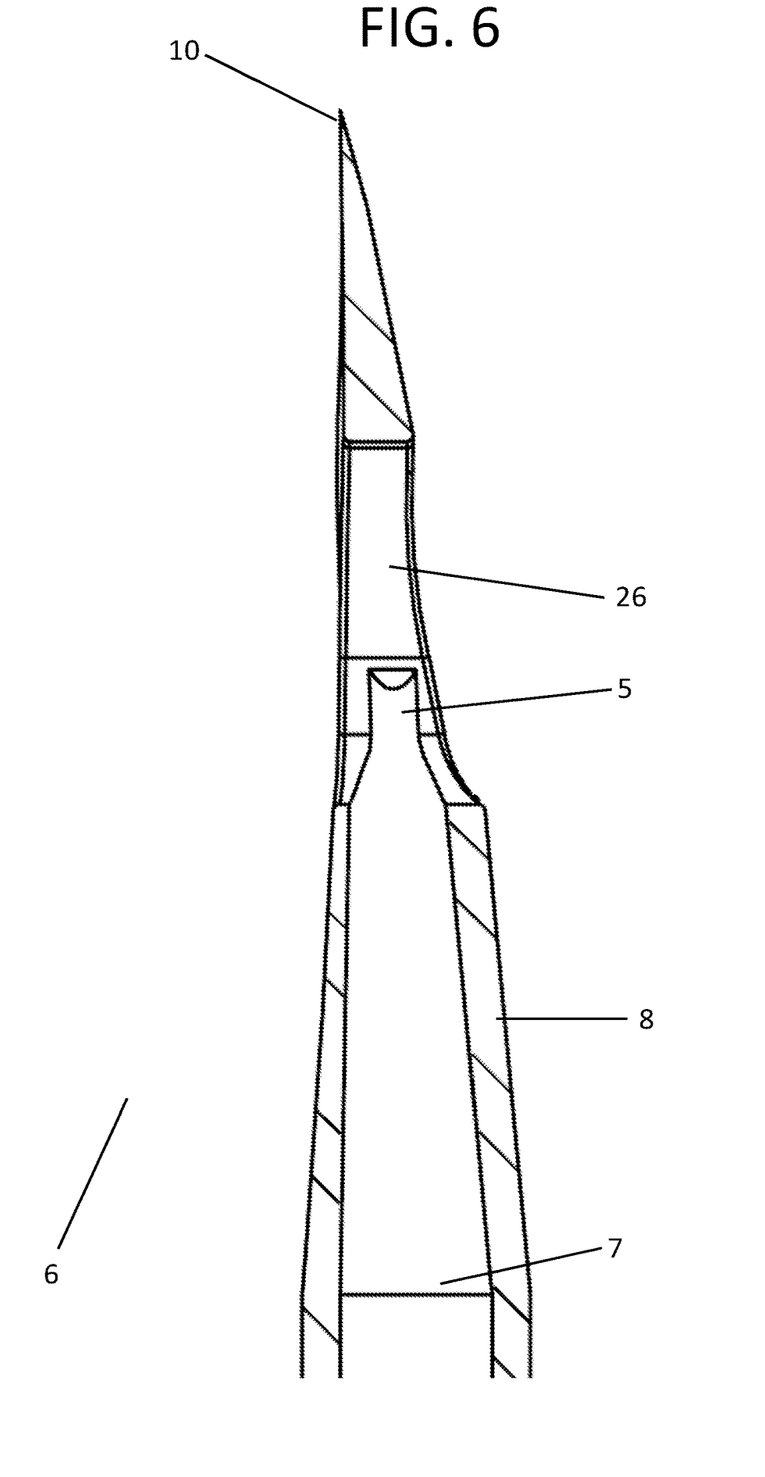
FIG. 6 illustrates an enlarged side cross sectional view of the distal end of the hypodermic injection needle along line A-A of FIG. 4.
Figure 7:
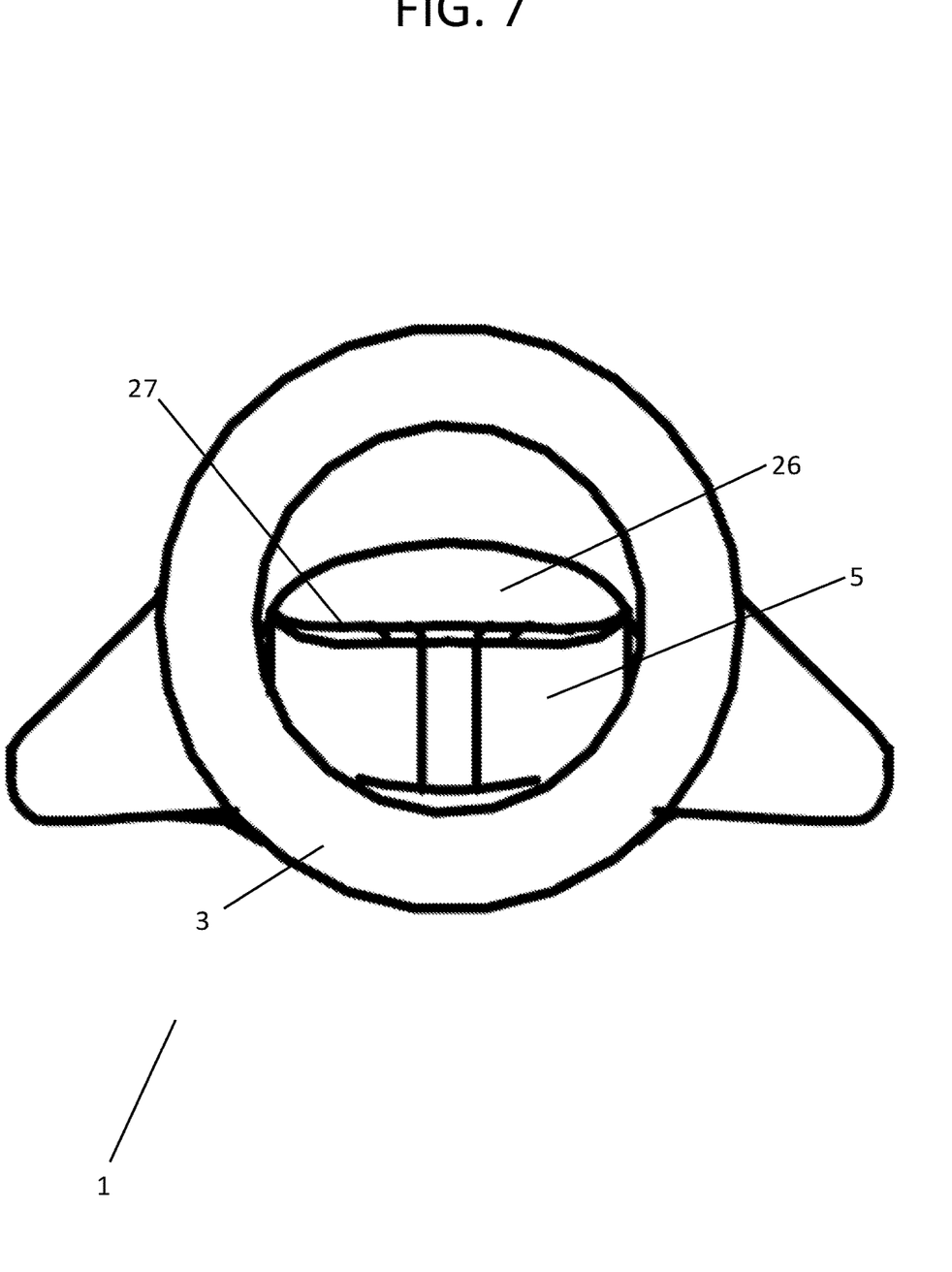
FIG. 7 illustrates a rear view of the hypodermic injection needle.
Figure 8:
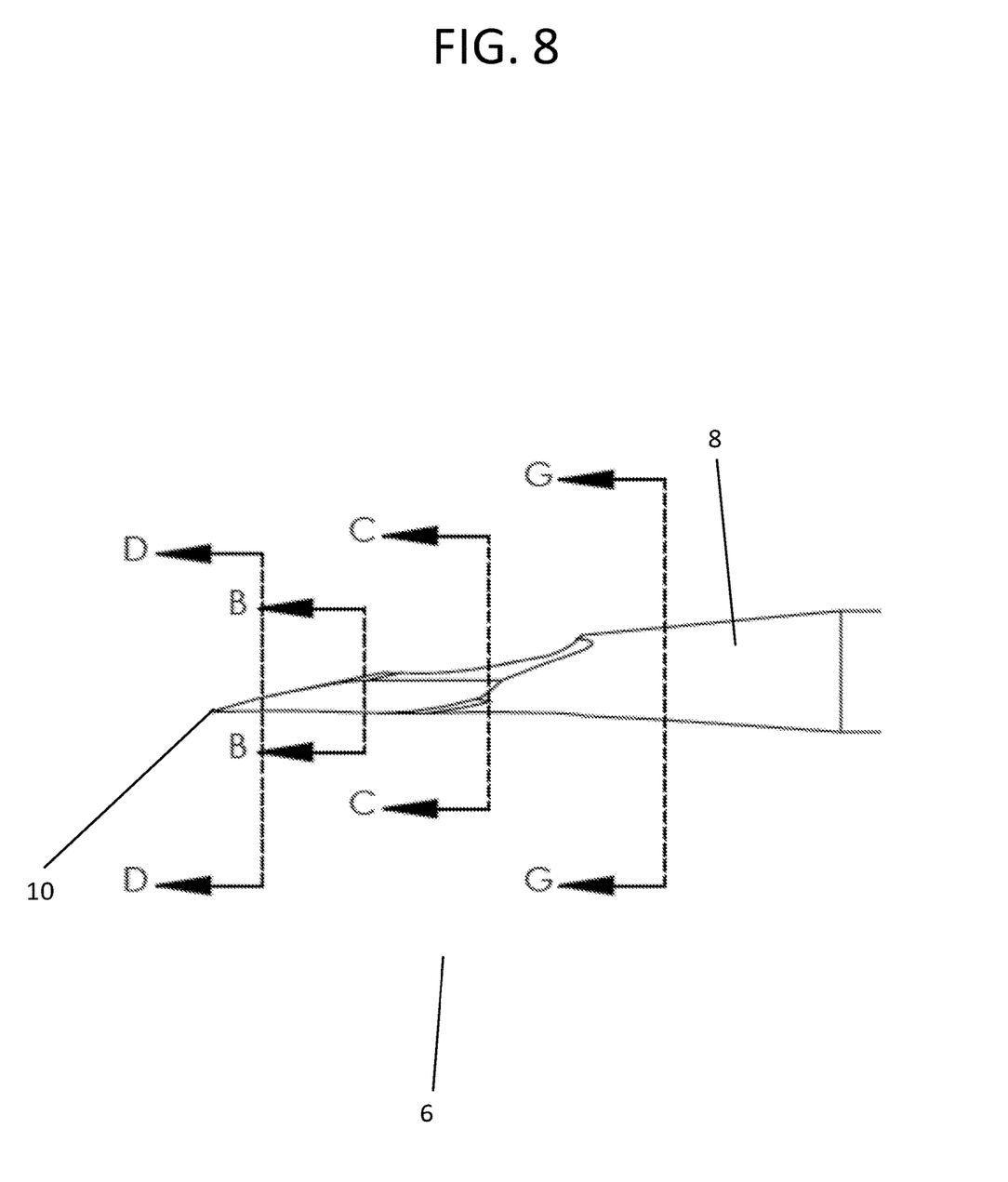
FIG. 8 illustrates an enlarged side view of the distal end of the hypodermic injection needle.
Figure 9:
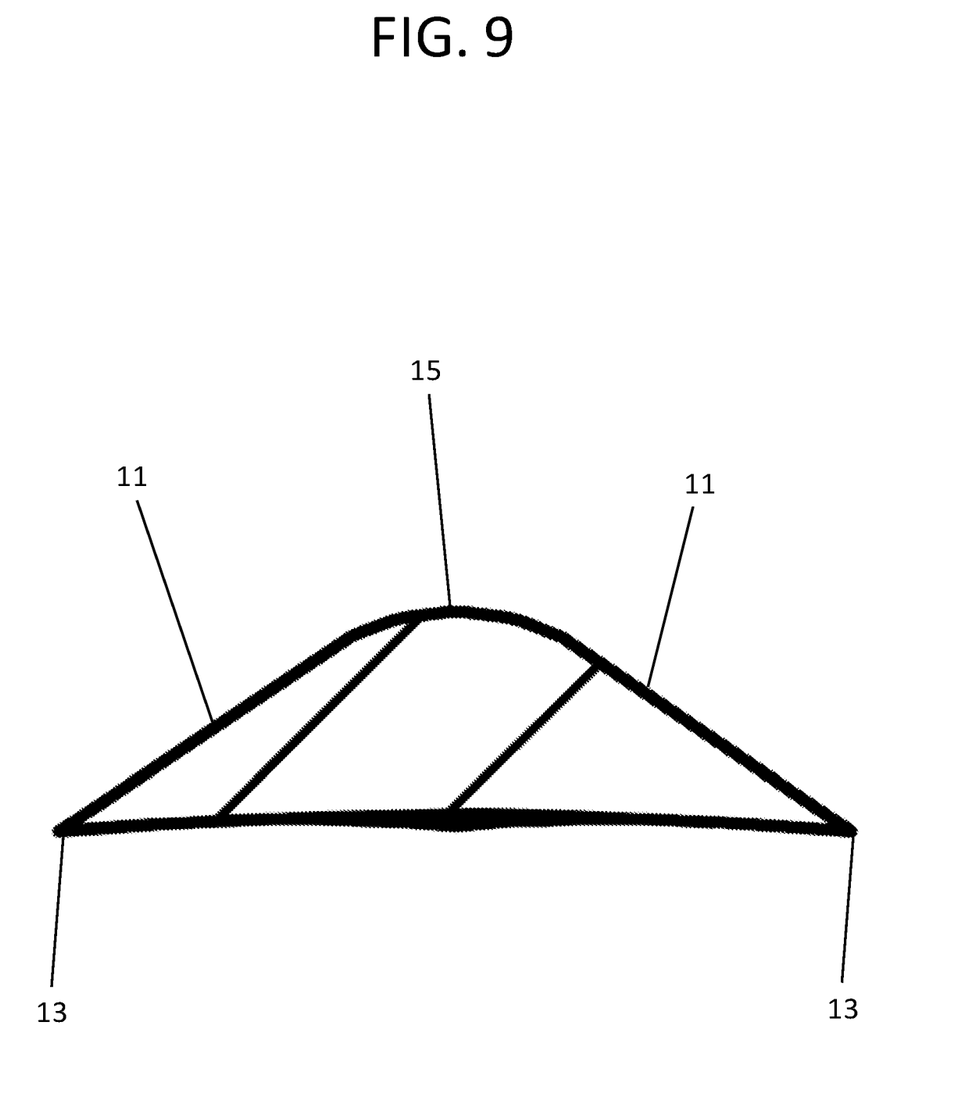
FIG. 9 illustrates an enlarged front cross sectional view of the hypodermic injection needle along line B-B of FIG. 8.
Figure 10:
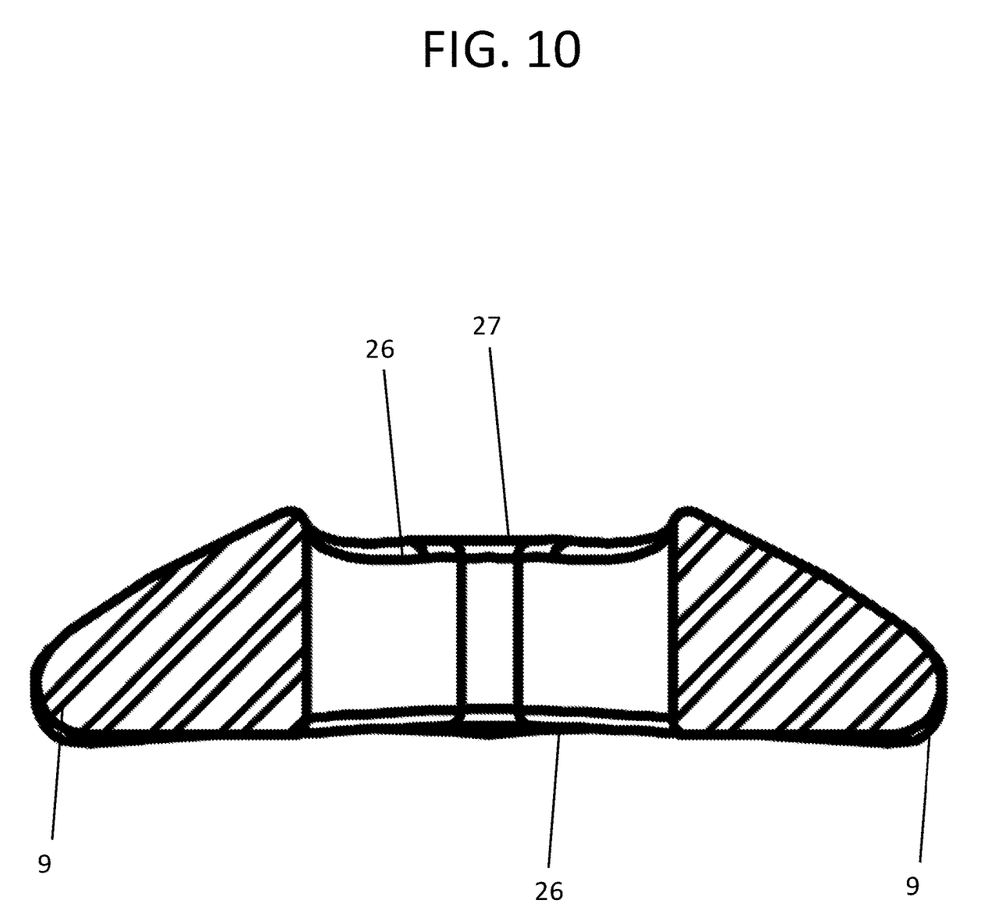
FIG. 10 illustrates an enlarged front cross sectional view of the hypodermic injection needle along line C-C of FIG. 8.
Figure 11:
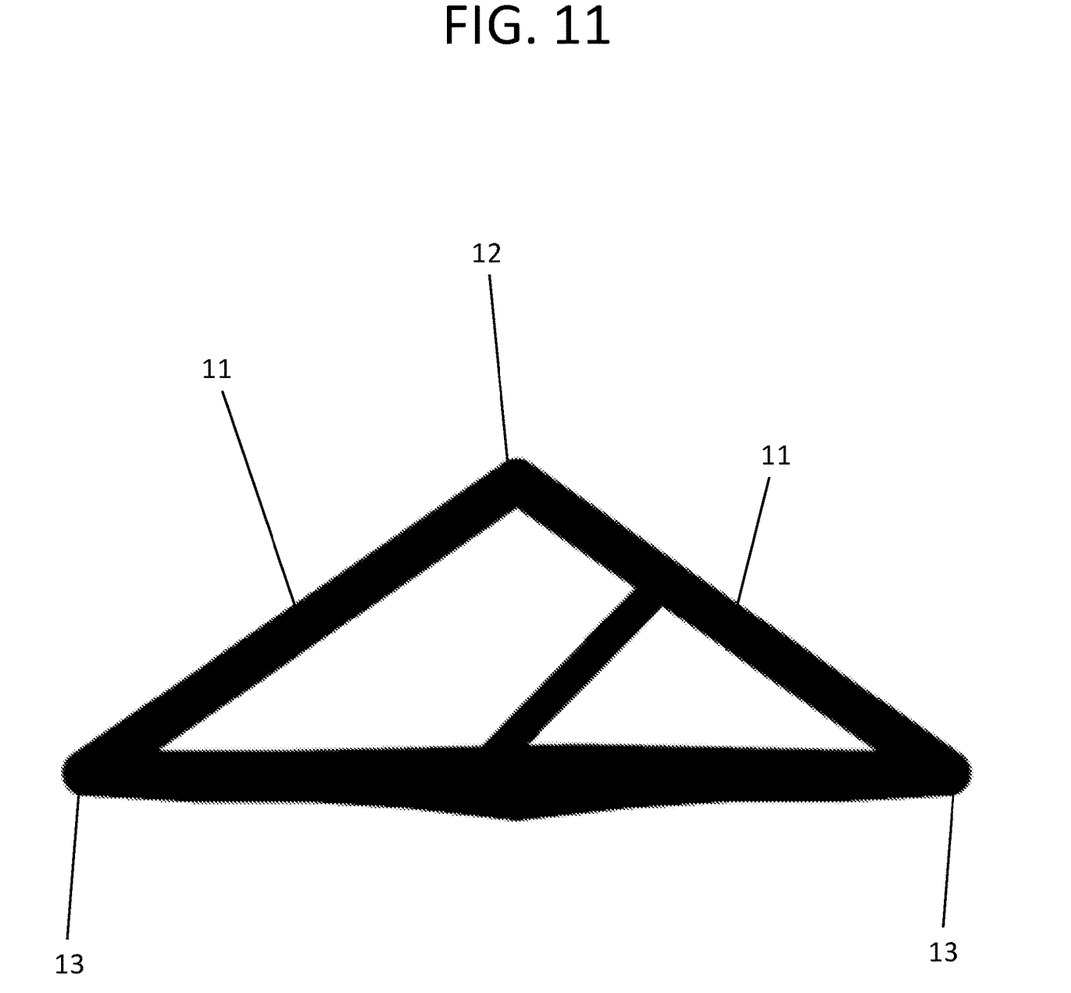
FIG. 11 illustrates an enlarged front cross sectional view of the hypodermic injection needle along line D-D of FIG. 8.
Figure 12:
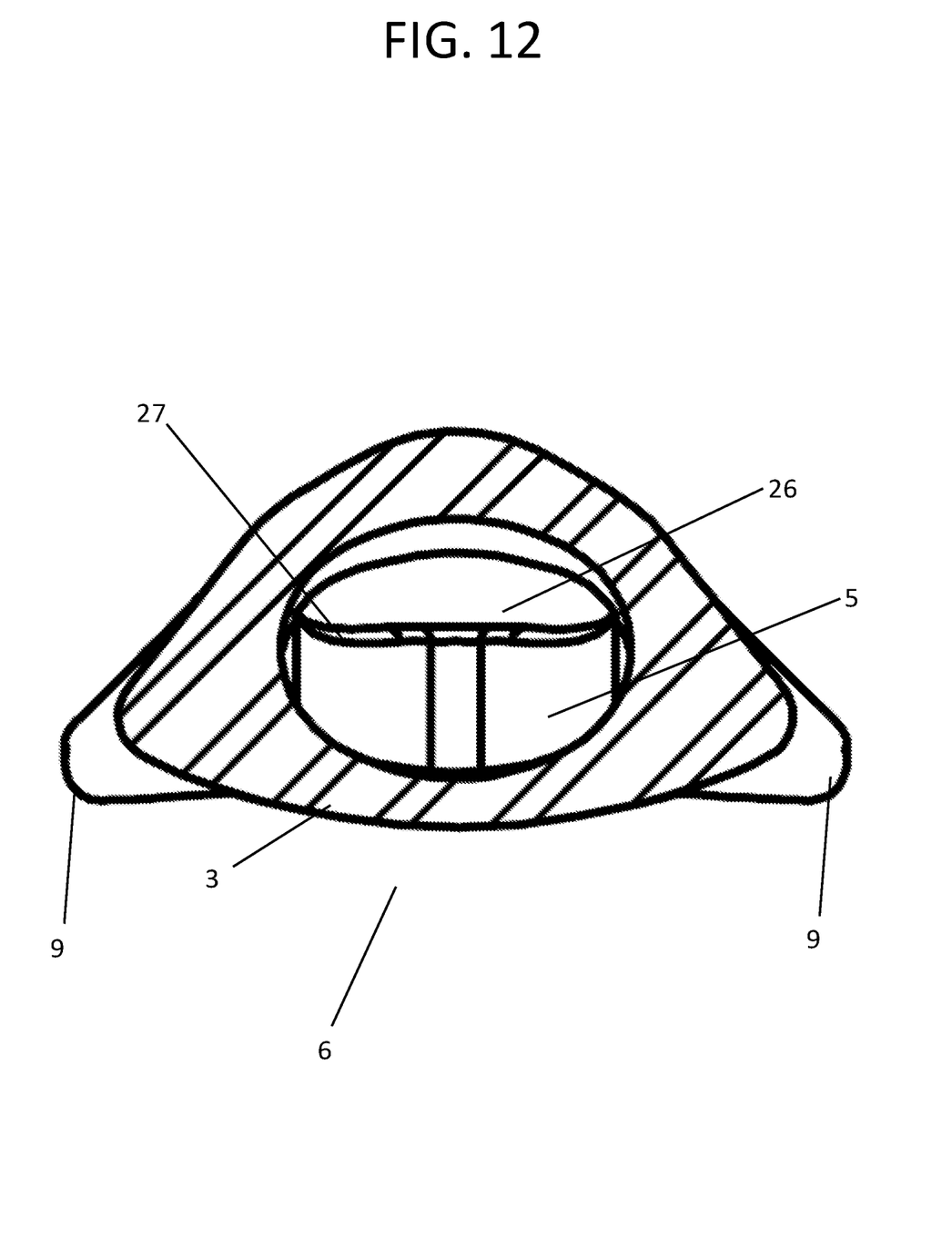
FIG. 12 illustrates an enlarged front cross sectional view of the hypodermic injection needle along line G-G of FIG. 8.

The two primary surfaces 11 each comprise outward distal edges 13 that extenting outwardly from the apex 10. The outward distal edges 13 are substantially symmetrically with each other. The outward distal edges 13 gradually curve outwardly from the apex 10 to a width greater than the tube 3, and then the edges 13 curve towards the central axis 4 as they reach the tissue penetration line 9 on the multi-surface distal end 6. The two primary surfaces 11 further comprise proximal edges 14 that intersect with expanding tube 8. The proximal edges 14 are substantially symmetrical with each other. As illustrated in FIG. 11, the two primary surfaces 11, the first intersect edge 12, and the apex 10 form a cross section that is substantially triangular-shaped.

The multi-surface distal end 6 of the needle 1 also comprises a secondary central surface 15 between the two primary surfaces 11 in front of top fluid opening 26. In embodiments of the subject invention, the secondary central surface 15 may be substantially flat or gradually curved. The secondary central surface 15 and the two primary surfaces 11 meet at a first intersect point 16 at the proximal end of first intersect edge 12. The first intersect point 16 is substantially aligned with the central axis 4.

The secondary central surface 15 and the two primary surfaces 11 each contain a second intersect edge 17 that extends proximally from the first intersect point 16. The proximal end of the secondary central surface 15 forms part of the curved border 27 with the top fluid opening 26. As illustrated in FIG. 18, the two primary surfaces 11, the secondary central surface 15, and the second intersect edges 17 form a cross section that is substantially trapezoidal-shaped.

The multi-surface distal end 6 of the needle 1 also comprises two tertiary surfaces 18 extending proximally on opposing sides from the secondary central surface 15 and the two primary surfaces 11, about the top fluid opening 26. The two tertiary surfaces 18 are substantially symmetrical with each other on either side of the multi-surface distal end 6. In embodiments of the subject invention, the two tertiary surfaces 18 may be substantially flat or gradually curved.

The secondary central surface 15 and the two tertiary surfaces 18 each contain a third intersect edge 19. The two primary surfaces 11 and the two tertiary surfaces 18 each contain a fourth intersect edge 20. The internal side of each tertiary surface 18 forms part of the curved border 27 with the top fluid opening 26.

The two tertiary surfaces 18 further comprise proximal edges 21 that intersect with expanding tube 8.

The multi-surface distal end 6 of the needle 1 also comprises two quaternary surfaces 22 extending proximally on opposing sides from the two primary surfaces 11. The two quaternary surfaces 22 are substantially symmetrical with each other on either side of the multi-surface distal end 6. In embodiments of the subject invention, the two quaternary surfaces 22 may be substantially flat or gradually curved. The two quaternary surfaces 22 each comprise outward distal edges 23 that extend along the central axis 4. The outward distal edges 23 are substantially symmetrically with each other. The two primary surfaces 11 and the two quaternary surfaces 22 each contain a fifth intersect edge 24. The two quaternary surfaces 22 further comprise proximal edges 25 that intersect with expanding tube 8. The proximal edges 25 are substantially symmetrical with each other.

The multi-surface distal end 6 of the needle 1 contains two fluid openings 26 on opposing sides. The fluid openings 26 are substantially symmetrically with each other and contain a curved border 27. The fluid openings 26 are substantially aligned with the central axis 4. The fluid openings 26 are in fluid communication on the proximal end with the internal fluid-carrying lumen 5 of tube 3.

During use, the multi-surface distal end 6 of needle 1 penetrates the soft tissue at apex 10. As apex 10 is pushed into the tissue, the outward distal edges 13, the first intersect edge 12, and the two primary surfaces 11 stretch, but do not cut, the soft tissue penetrated by the apex 10. As the needle 1 is pushed further into the tissue, the gradual curve outwards of the distal edges 13 stretch the tissue. The secondary central surface 15, the first intersect point 16, the second intersect edges 17, the two tertiary surfaces 18, the third intersect edges 19, the fourth intersect edges 20, the two quaternary surfaces 22, the outward distal edges 23, and the fifth intersect edges 24 all stretch the tissue further until the tissue penetration line 9 on the multi-surface distal end 6 penetrates the tissue and the fluid openings 26 are within the tissue. The fluid openings 26 inject fluid into the tissue on opposing sides from the internal fluid-carrying lumen 5 of tube 3.

The multi-surface distal end 6 of needle 1 stretches soft tissue with minimal cutting to reduce patient discomfort or pain. The structure of the multi-surface distal end 6 of the needle 1 reduces the force required for urging the multi-surface distal end 6 into the soft tissue. The structure of the multi-surface distal end 6 of the needle 1 also prevents soft tissue coring. The structure of the multi-surface distal end 6 substantially decreases the penetration footprint of the needle 1 into the soft tissue around the needle penetration site, substantially reducing tissue inflammation and increasing healing time. This tissue stretching eliminates soft tissue coring and substantially decreases the penetration footprint of the needle 1 into the soft tissue around the needle penetration site from apex 10.

The simultaneous injection of fluid from the fluid openings 26 on opposing sides discharges injected fluid over a wider area with a lower pressure.

The proximal end 2 of the injection needle 1 may be attached to any conventional injection syringe assembly as known to those skilled in the art. Such as the syringe assembly having a generally tubular barrel portion including a reduced diameter tip portion with the needle 1 affixed by any suitable means to the tip portion of the barrel, such that the lumen through the needle is in fluid communication with the interior of the syringe barrel. The syringe barrel typically includes a radial flange at its open end which receives a stopper assembly, including a plunger rod and a stopper. As will be understood by those skilled in this art, the stopper forms a sealed fit with the interior surface of the syringe barrel such that as the plunger is reciprocated through the barrel, a fluid may be may be injected into a patient through the needle 1.

What is claimed is:

1. A medical needle for penetrating soft tissue and dispensing fluid, the needle comprising:
   a proximal end tube with a central axis comprising an internal fluid-carrying lumen,
   a multi-surface distal end comprising a soft tissue penetrating apex substantially aligned with the central axis;
   two primary surfaces extending proximally from the apex, wherein the primary surfaces are substantially symmetrical with each other and formed on opposing sides of the apex about the central axis, wherein the two primary surfaces comprise outward edges;
   a first intersect edge extending proximally from the apex and connecting the two primary surfaces, wherein the first intersect edge is substantially aligned with the central axis;
   a secondary central surface directly proximal from the first intersect edge and between the two primary surfaces, wherein the secondary central surface and the two primary surfaces are connected at a first intersect point and two second intersect edges demarcating planes of the secondary central surface and planes of the two primary surfaces,
   a top fluid opening directly proximal from the secondary central surface, wherein the top fluid opening extends to a bottom fluid opening, wherein the top and bottom fluid openings are substantially aligned and are in fluid communication with the internal fluid-carrying lumen of the tube;
   two tertiary surfaces on opposing sides of the top fluid opening about the central axis, wherein the tertiary surfaces are substantially symmetrical with each other, wherein the two tertiary surfaces and the two primary surfaces are connected at fourth intersect edges demarcating planes of the two tertiary surfaces and planes of the two primary surfaces, further wherein the two tertiary surfaces and the secondary central surface are connected at the two second intersect edges demarcating the planes of the two tertiary surfaces and planes of the secondary central surface;
   wherein the multi-surface distal end of the needle is configured to stretch the soft tissue at a penetration point of the apex as the needle is inserted into the soft tissue; and
   wherein the distal end of the needle is configured to be inserted into the soft tissue until the top and bottom fluid openings are within the soft tissue, wherein fluid is configured to be injected from the internal fluid-carrying lumen of the tube simultaneously through the top and bottom fluid openings into the soft tissue.

2. The medical needle of claim 1, wherein a distal end of the tube expands outwardly in a distal direction.

3. The medical needle of claim 1, wherein the distal end of the needle is configured to stretch penetrated tissue 0.3 to 0.6 inches.

4. The medical needle of claim 1, wherein the distal end of the needle is configured to stretch penetrated tissue 0.3 to 0.6 cm.

5. The medical needle of claim 1, wherein the distal end of the needle comprises a substantially trapezoidal-shaped cross section that forms into a substantially triangular-shaped cross section in a distal direction.

6. The medical needle of claim 1, wherein the two primary surfaces comprise gradually curved surfaces.

7. The medical needle of claim 1, wherein the multi-surface distal end of the needle is configured not to cut the soft tissue after the apex penetrates the soft tissue and the needle is inserted.

8. The medical needle of claim 1, wherein the two primary surfaces, the outward edges of the two primary surfaces, the first intersect edge, the secondary central surface, the first intersect point, the two second intersect edges, the two tertiary surfaces, two third intersect edges, and the fourth intersect edges all are configured not to cut the soft tissue after the apex penetrates the soft tissue and the needle is inserted.

9. The medical needle of claim 1, wherein the multi-surface distal end of the needle is configured not to core the soft tissue after the apex penetrates the soft tissue and the needle is inserted.

10. The medical needle of claim 1, wherein the two primary surfaces, the outward edges of the two primary surfaces, the first intersect edge, the secondary central surface, the first intersect point, the two second intersect edges, the two tertiary surfaces, two third intersect edges, and the fourth intersect edges all are configured not to core the soft tissue after the apex penetrates the soft tissue and the needle is inserted.

11. The medical needle of claim 1, further comprising two quaternary surfaces on opposing sides of the fluid openings about the central axis, wherein the two quaternary surfaces are substantially symmetrical with each other;
   wherein the two quaternary surfaces and the two primary surfaces are connected at fifth intersect edges demarcating planes of the two quaternary surfaces and the planes of the two primary surfaces,
   wherein the two primary surfaces, the outward edges of the two primary surfaces, the first intersect edge, the secondary central surface, the first intersect point, the two second intersect edges, the two tertiary surfaces, two third intersect edges, the fourth intersect edges, the two quaternary surfaces, and the fifth intersect edges all are configured to stretch the soft tissue at a penetration point of the apex as the needle is configured to be inserted into the soft tissue; and
   wherein the distal end of the needle is configured to be inserted into the soft tissue until the top and bottom fluid openings are within the tissue, wherein fluid is configured to be injected from the internal fluid-carrying lumen of the tube simultaneously through the top and bottom fluid openings into the soft tissue.

12. A medical needle for penetrating soft tissue and dispensing fluid, the needle comprising:
- a proximal end tube with a central axis comprising an internal fluid-carrying lumen,
- a multi-surface distal end comprising a soft tissue penetrating apex substantially aligned with the central axis;
- two primary surfaces extending proximally from the apex, wherein the primary surfaces are substantially symmetrical with each other and formed on opposing sides of the apex about the central axis, wherein the two primary surfaces comprise curved edges extending outwardly from the central axis, further wherein the curved edges extend to a width greater than a width of the tube;
- a first intersect edge extending proximally from the apex and connecting the two primary surfaces, wherein the first intersect edge is substantially aligned with the central axis;
- a secondary central surface directly proximal from the first intersect edge and between the two primary surfaces, wherein the secondary central surface and the two primary surfaces are connected at a first intersect point and two second intersect edges demarcating planes of the secondary central surface and planes of the two primary surfaces,
- a top fluid opening directly proximal from the secondary central surface, wherein the top fluid opening extends to a bottom fluid opening, wherein the top and bottom fluid openings are substantially aligned and are in fluid communication with the internal fluid-carrying lumen of the tube;
- two tertiary surfaces on opposing sides of the top fluid opening about the central axis, wherein the tertiary surfaces are substantially symmetrical with each other, wherein the two tertiary surfaces and the two primary surfaces are connected at two fourth intersect edges demarcating planes of the two tertiary surfaces and planes of the two primary surfaces, further wherein the two tertiary surfaces and the secondary central surface are connected at two third intersect edges demarcating planes of the two tertiary surfaces and planes of the secondary central surface;
- wherein the two primary surfaces, the curved edges of the two primary surfaces, the first intersect edge, the secondary central surface, the first intersect point, the two second intersect edges, the two tertiary surfaces, the two third intersect edges, and the two fourth intersect edges all are configured to stretch the soft tissue at a penetration point of the apex as the needle is into inserted into the soft tissue; and
- wherein the distal end of the needle is configured to be inserted into the soft tissue until the top and bottom fluid openings are within the soft tissue, wherein fluid is configured to be injected from the internal fluid-carrying lumen of the tube simultaneously through the top and bottom fluid openings into the soft tissue.

* * * * *